(12) United States Patent
Abi-Samra et al.

(10) Patent No.: US 9,453,839 B2
(45) Date of Patent: Sep. 27, 2016

(54) MICROFLUIDIC DEVICE, MICROFLUIDIC SYSTEM AND METHOD FOR CONTROLLING MICROFLUIDIC TEST DEVICE

(71) Applicants: SAMSUNG ELECTRONICS CO., LTD., Suwon-si (KR); ULSAN NATIONAL INSTITUTE OF SCIENCE AND TECHNOLOGY, Ulsan (KR)

(72) Inventors: Kameel Abi-Samra, Carlsbad, CA (US); Marc Madou, Irvine, CA (US); Tae Hyeong Kim, Yeongcheon-si (KR); Yoon-Kyoung Cho, Ulsan (KR)

(73) Assignees: SAMSUNG ELECTRONICS CO., LTD., Suwon-si (KR); ULSAN NATIONAL INSTITUTE OF SCIENCE AND TECHNOLOGY, Ulsan (KR)

( * ) Notice: Subject to any disclaimer, the term of this patent is extended or adjusted under 35 U.S.C. 154(b) by 155 days.

(21) Appl. No.: 14/068,363

(22) Filed: Oct. 31, 2013

(65) Prior Publication Data
US 2014/0120521 A1 May 1, 2014

(30) Foreign Application Priority Data
Oct. 31, 2012 (KR) .................... 10-2012-0122538

(51) Int. Cl.
*B01L 3/00* (2006.01)
*G01N 33/543* (2006.01)
*G01N 35/04* (2006.01)

(52) U.S. Cl.
CPC ..... *G01N 33/5438* (2013.01); *B01L 3/502746* (2013.01); *B01L 2200/143* (2013.01); *B01L 2300/0645* (2013.01);
(Continued)

(58) Field of Classification Search
CPC .................... G01N 33/5438; B01L 3/502746
See application file for complete search history.

(56) References Cited

U.S. PATENT DOCUMENTS 6,030,581 A * 2/2000 Virtanen ............... B01L 3/5027
369/275.1
6,063,589 A * 5/2000 Kellogg ............. B01F 13/0059
366/DIG. 3
(Continued)

FOREIGN PATENT DOCUMENTS

KR 10-2009-0083689 A 8/2009
KR 10-2011-0057416 A 6/2011

*Primary Examiner* — Melanie Y Brown
(74) *Attorney, Agent, or Firm* — Sughrue Mion, PLLC

(57) ABSTRACT

A microfluidic device, a microfluidic system and a method for controlling a microfluidic test device are provided. The microfluidic device includes a rotatable platform including a sample chamber to which a sample is supplied, a first reagent chamber; a first capture conjugate disposed in the first reagent chamber and configured to capture a target material contained in the sample; a second reagent chamber; a signal material disposed in the second reagent chamber and configured to be electrochemically induced by the first capture conjugate; a reaction chamber providing an area in which a biochemical reaction between the sample and the signal material supplied occurs when the platform rotates; a second capture material disposed in the reaction chamber and configured to capture the target material; a detection chamber separated from the reaction chamber, the detection chamber comprising a detector configured to detect an electrochemical signal generated by the signal material; and a plurality of channels connecting the chambers.

10 Claims, 16 Drawing Sheets

(52) U.S. Cl.
CPC . *B01L 2300/0803* (2013.01); *B01L 2300/087* (2013.01); *B01L 2300/0883* (2013.01); *B01L 2400/0409* (2013.01); *B01L 2400/084* (2013.01); *G01N 2035/0449* (2013.01)

(56) References Cited

U.S. PATENT DOCUMENTS

| | | | | |
|---|---|---|---|---|
| 6,143,247 A * | 11/2000 | Sheppard, Jr. | ...... | B01F 15/0233 210/109 |
| 6,391,558 B1 * | 5/2002 | Henkens | ............... | C12Q 1/6825 422/50 |
| 7,459,127 B2 * | 12/2008 | Pugia | .................... | B01L 3/5025 422/502 |
| 7,790,110 B2 * | 9/2010 | Cho | .................. | B01L 3/502753 422/506 |
| 8,062,611 B2 * | 11/2011 | Faulstich | .......... | B01L 3/502738 422/501 |
| 2008/0108095 A1 * | 5/2008 | Li | ..................... | B01L 3/502746 435/7.93 |
| 2015/0226735 A1 * | 8/2015 | Hodges | ................. | B01L 3/5027 435/7.92 |

* cited by examiner

MICROFLUIDIC DEVICE, MICROFLUIDIC SYSTEM AND METHOD FOR CONTROLLING MICROFLUIDIC TEST DEVICE

CROSS-REFERENCE TO RELATED APPLICATION(S)

This application claims priority from Korean Patent Application No. 10-2012-0122538, filed on Oct. 31, 2012 in the Korean Intellectual Property Office, the disclosure of which is incorporated herein by reference.

BACKGROUND

1. Field

Apparatuses and methods consistent with exemplary embodiments relate to a microfluidic device, a microfluidic system and a method for controlling a microfluidic test device, wherein a target material in a sample is detected using an electrochemical sensor.

2. Description of the Related Art

A microfluidic device handles a small amount of fluid using a microfluidic structure such as a chamber or channel formed on a platform, and detects specific results by inducing biological or chemical reactions of the fluid.

In general, a microfluidic structure which performs a single independent function in a microfluidic device includes a chamber to accommodate a fluid, a channel to enable the fluid to flow, and a device to control flow of the fluid, and may be implemented as a variety of combinations thereof. A device which includes such a microfluidic structure disposed on a chip-type substrate and performs several processes including treatment and operations in order to perform tests including immune-serum reactions or biochemical reactions on a small chip is referred to as a "lab-on-a-chip."

In recent years, techniques associated with a lab-on-a-chip combined with an electrochemical sensor capable of improving user convenience and acquiring high sensitivity have been developed. Techniques developed to date have problems in that an analysis process requires a long time and skilled engineers, and reaction between a target material and a capture material occurs in a chamber accommodating an electrochemical sensor, and various biochemical molecules are thus non-specifically bonded to the surface of electrodes, thus disadvantageously causing deterioration in performance of the sensor.

SUMMARY

Exemplary embodiments provide a microfluidic device and a microfluidic system which establish a system to automate an overall process of electrochemical immunoassay and realize simple and accurate electrochemical immunoassay.

One or more exemplary embodiments provide a microfluidic device and a microfluidic system wherein a surface of a sensor is used for detection by physically separating a chamber in which reactions occur from a chamber in which electrochemical sensing occurs, and thereby obtaining accurate results with high sensitivity by detecting signals resulting from fluid flow created by rotating the microfluidic device.

One or more exemplary embodiments also provide a microfluidic system and a method for controlling a microfluidic test device which calculates a flow rate of a fluid which passes through an electrochemical sensor using a detected signal.

In accordance with an aspect of an exemplary embodiment, there is provided a microfluidic device including a rotatable platform, wherein the platform includes a sample chamber into which a sample is supplied, a first reagent chamber; a first capture conjugate disposed in the first reagent chamber and configured to capture a target material contained in the sample; a second reagent chamber; an electrochemically activated signal material disposed in the second reagent chamber and configured to induce electrochemical activity of the signal material; a reaction chamber; a second capture material disposed in the reaction chamber and configured to capture the target material, the reaction chamber providing an area in which a biochemical reaction between the sample and the signal material supplied occurs when the platform rotates; a detection chamber separated from the reaction chamber, the detection chamber comprising a detector configured to detect an electrochemical signal generated by the signal material; and a plurality of channels connecting the chambers.

The first capture conjugate may be a conjugate of the first capture material configured to capture the target material and an activity-inducing material configured to induce electrochemical activity of the signal material.

The second capture material may be immobilized within the reaction chamber.

The second capture material may be immobilized on an inner wall of the reaction chamber.

The second capture material may be immobilized on a bead or particle disposed within the reaction chamber.

The signal material may be a material which is oxidized or reduced by the activity-inducing material.

The detector may include a plurality of electrodes and an electrochemical sensor configured to detect an electrochemical signal from an oxidation/reduction reaction occurring in at least one of the electrodes.

The detector may include a detection portion contacting a reaction solution flowing in the detection chamber and configured to detect an electrochemical signal, and a connection portion configured to transfer the electrochemical signal detected by the detection portion to the outside.

The detection portion may be disposed inside the detection chamber and the connection portion may be disposed outside the detection chamber.

The detection portion of the detection chamber may have a width which is greater than a width of an inlet through which the reaction solution is supplied, and greater than a width of an outlet through which the reaction solution is discharged.

At least one of the channels may have a shape providing a high flow resistance.

In accordance with an aspect of another exemplary embodiment, there is provided a microfluidic system including a microfluidic device including a rotatable platform and an electrochemical sensor formed on the platform, a motor configured to rotate the platform, and a slip ring mounted on the motor and electrically connected to the electrochemical sensor.

The electrochemical sensor may include a detection portion configured to detect a signal, and a connection portion configured to transfer the detected signal to the slip ring.

The microfluidic device may further include a printed circuit board (PCB) configured to electrically connect the slip ring to the connection portion.

The microfluidic system may further include a brush contacting the slip ring and configured to supply electricity.

The electrochemical sensor may be configured to receive electricity through the slip ring, detect a signal using the supplied electricity, and transfer the signal to the slip ring.

The microfluidic system may further include a controller configured to control rotation of the platform, supply the electricity, receive the detected signal from the slip ring, and perform processing on the signal.

The controller may be configured to supply electricity to the electrochemical sensor while rotating the platform and determine a presence or an amount of the target material in a fluid supplied to the microfluidic device based on the signal detected by the electrochemical sensor.

The controller may be configured to supply electricity to the electrochemical sensor while rotating the platform and calculate a flow rate of the fluid supplied to the microfluidic device based on the signal detected by the electrochemical sensor.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
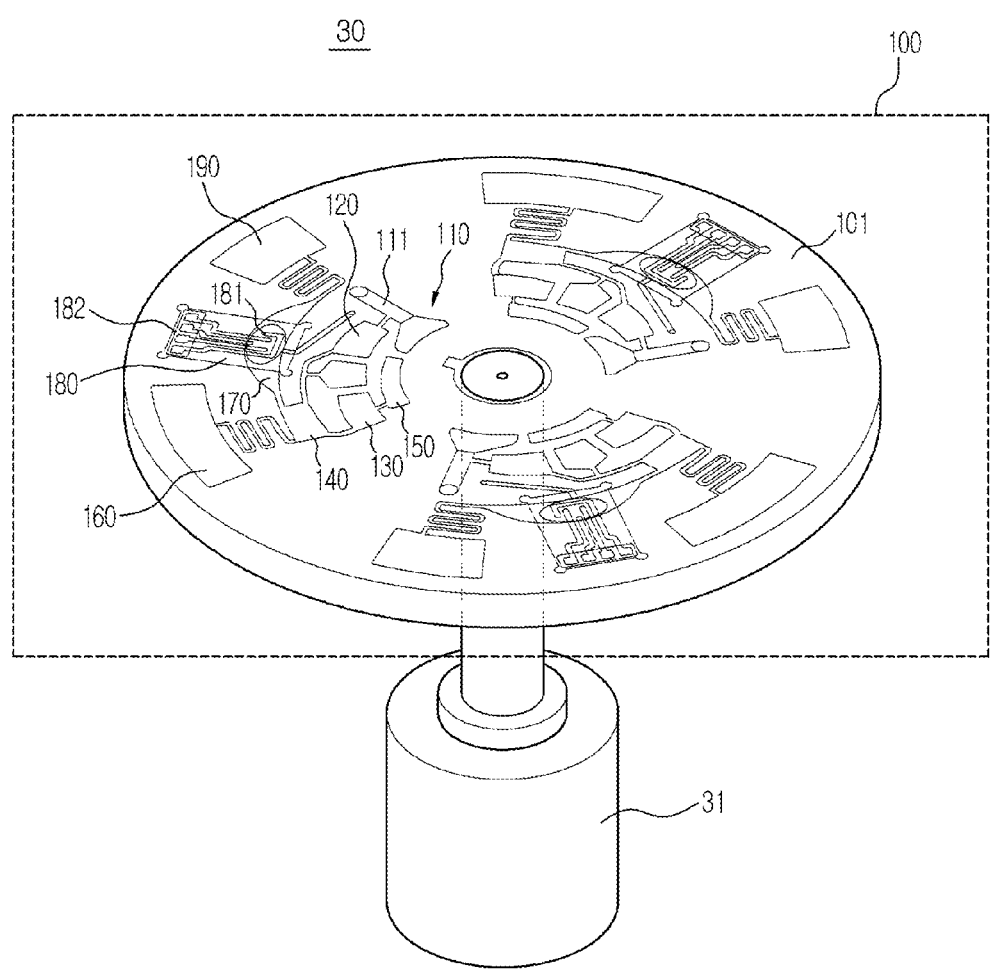
FIG. 1 is a perspective view illustrating a configuration of a microfluidic device according to an exemplary embodiment.

Reference will now be made in detail to exemplary embodiments, examples of which are illustrated in the accompanying drawings, wherein like reference numerals refer to like elements throughout.

Hereinafter, a microfluidic device according to an exemplary embodiment will be described in detail with reference to the annexed drawings.

FIG. 1 is a perspective view illustrating a configuration of a microfluidic device according to an exemplary embodiment.

Referring to FIG. 1, the microfluidic device 100 includes a platform 101 on which a variety of microfluidic structures are formed.

Each microfluidic structure includes a plurality of chambers configured to accommodate fluids and a plurality of channels connecting the chambers.

The term "microfluidic structure" used herein does not refer to a structure with a specific shape, but rather, broadly refers to a structure which includes a plurality of chambers and a plurality of channels connecting the chambers and is formed on the microfluidic device. The microfluidic structure may be configured to perform different functions according to the dispositions of the chambers and channels, and/or the types of fluids contained in the chambers or flowing within the channels.

The platform 101 is made of a material which is easy to form and has a biologically inactive surface. In various exemplary embodiments, the platform 101 is made from any of a variety of materials including plastic materials such as polymethyl methacrylate (PMMA), PDMS, PC, polypropylene, polyvinylalcohol, and polyethylene, glass, mica, silica, and silicone wafer. These materials are given only as examples of materials which may be used for the platform 101 and any material may be used for the platform 101 so long as it has chemical and biological stability, optical transparency and mechanical processability.

The platform 101 may include two or more layers of plates. Thus, in various exemplary embodiments, a groove corresponding to a microfluidic structure such as a chamber or channel is formed on a surface at which two plates contact each other and the two plates are thereafter bonded to each other, thereby forming an area accommodating fluids and one or more passages enabling the fluids to flow to within the platform 101. The bonding between the plates may be carried out by a variety of methods such as adhesion using an adhesive or a double-sided tape, ultrasonic fusing or laser welding.

In FIG. 1, an upper surface of the platform 101 is not illustrated in order to represent the microfluidic structure formed on the platform 101.

The microfluidic device 100 is shown mounted on a microfluidic test device 30 including a driver 31 and rotates using power supplied from the driver 31. Thus, the microfluidic test device 30 is configured to control movement of fluids using centrifugal force generated by rotation of the microfluidic device 100.

The fluid is transferred from a chamber close to the center of the platform 101 to a chamber closer to an outer edge of the platform 101 based on centrifugal force and flow of the fluid is controlled by opening or closing a valve provided in the channel connecting the chambers.

In the exemplary embodiment, various forms of microfluidic valves may be used. A valve such as a capillary tube valve which passively opens when a predetermined level of pressure is applied, or a valve which receives power or energy (for example, magnetic energy or thermal energy) from the outside by a driving signal to actively operate may be used.

In an exemplary embodiment using the latter valve, the valve may be formed from a phase transition material which exists in a solid state at room temperature and is melted at a high temperature. Thus, when the valve material is present in a solidified state in an inlet of the channel or chamber, it blocks the channel, and when the valve material receives energy from the outside, it melts and opens the channel.

Examples of useful valve materials include, but are not limited to, thermoplastic resins such as cyclic olefin copolymers (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), and polyvinylidene fluoride (PVDF), and waxes such as paraffin wax, microcrystalline wax, synthetic wax and natural wax.

In addition, a plurality of fine heating particles which absorb electromagnetic energy and emit heat may be dispersed within the valve material. The fine heating particles may have a diameter of about 1 nm to about 100 μm, to enable the fine heating particles to freely pass through fine channels having a depth of about 0.1 mm and a width of 1 mm. The fine heating particles are homogeneously dispersed in the valve material, and rapidly increase in temperature and emit heat when electromagnetic energy is supplied by lasers or the like. In order to impart these properties to the fine heating particles, the fine heating particles may have a core containing a metal component and a hydrophobic surface structure.

Specifically, the fine heating particles may have a molecular structure including a core made of Fe and a plurality of surfactants bonded to and surrounding the Fe. The fine heating particles may be dispersed in a carrier oil for storage. The carrier oil may be hydrophobic so as to homogeneously disperse the fine heating particles having a hydrophobic surface structure. The carrier oil containing the fine heating particles dispersed therein is poured into the melted phase-transition material, followed by mixing. The mixed material is injected into an inlet of the channel or chamber and is solidified to block the inlet of the channel or chamber. The fine heating particles may be polymer particles and may be quantum dots or magnetic beads.

In addition, the fine heating particles may be formed from micro metal oxides such as, but no limited to, $Al_2O_3$, $TiO_2$, $Ta_2O_3$, $Fe_2O_3$, $Fe_3O_4$ or $HfO_2$.

Examples of the energy irradiated from the outside include electromagnetic energy. The outside energy source may be selected according to the wavelength of electromagnetic waves which may be absorbed by heating particles contained in the valve material. The energy source may be a laser light source configured to irradiate laser beams, a light emitting diode configured to irradiate visible light or infrared light or a Xenon lamp.

However, it should be understood that the valve according to the exemplary embodiment does not necessarily contain fine heating particles, and may therefore be made from only a phase-transition material. In this case, a heater which is spaced from the microfluidic device by a predetermined distance is used to heat the corresponding valve requiring opening in order to melt the valve material.

However, the microfluidic device according to an exemplary embodiment may not include a valve in the inlet of the chamber or the channel, and may therefore rely upon a method of controlling flow of the fluid without using the valve.

In the exemplary embodiment shown in FIG. 1, a circle-shaped disc type platform 100 is provided. The platform 101 may have a rotatable circular plate shape, a rotatable fan shape that is mounted on a rotatable frame, or a polygonal shape so long as it may be rotated by power supplied from a driver 31.

A platform 101 may be provided with a single test unit, but for increased throughput and cost efficiency, a platform 101 may be divided into a plurality of regions, each containing independent microfluidic structures, as shown in FIG. 1. In addition, as shown in FIG. 1, one sample chamber 110 may be provided in each test unit, or a plurality of test units may receive samples from a single sample chamber. A detailed explanation of the microfluidic structure shown in FIG. 1 will be given with reference to FIG. 2 below.

Figure 2:
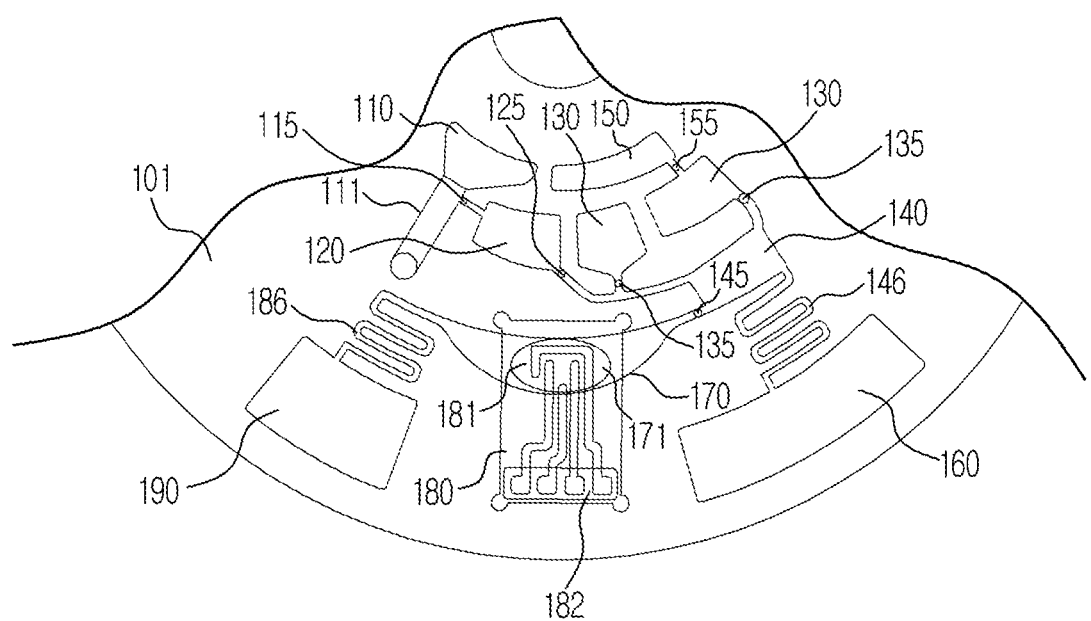
FIG. 2 is a plan view illustrating a part of a platform of the microfluidic device according to an exemplary embodiment, as seen from the top.

FIG. 2 is a plan view illustrating a part of a platform 101 of the microfluidic device 100 according to an exemplary embodiment, as seen from the top.

The microfluidic structure shown in FIG. 2 constitutes one test unit. As such, one or more test units which are the same as or different from the test unit shown in FIG. 2 may be formed or not formed in a non-illustrated part of the platform 101.

A method for detecting a target material contained in a sample using a microfluidic device includes an optical method, an electrochemical method or the like. The microfluidic device 100 according to an exemplary embodiment uses an electrochemical method to detect a target material contained in a sample.

Referring to FIG. 2, the platform 101 includes a sample chamber 110 into which a sample is injected, a first reagent chamber 120 containing a primary capture conjugate which specifically binds to a target material contained in the sample and activates generation of an electrochemical signal, a reaction chamber 140 in which the target material specifically binds to a secondary capture material, a second reagent chamber 150 configured to supply a signal material to the reaction chamber 140, and a detection chamber 170 configured to detect an electrochemical signal.

Hereinafter, a configuration and an operation of the microfluidic device 100 shown in FIG. 2 will be described in detail. The microfluidic device 100 operates while being mounted on the microfluidic test device 30 (see FIG. 1). In the exemplary embodiment of FIG. 2, at least one valve is provided in a channel connecting the chambers to control flow of the fluid. Accordingly, movement of the fluid between the chambers is carried out by rotation of the microfluidic device and opening of the at least one valve.

The sample chamber 110 is provided with a sample inlet (not shown) through which the sample is injected. The injected sample may be a bio-sample such as blood, bodily fluids such as lymph fluids or tissue fluids and urine, or an environmental sample to control water or soil. However, any fluid may be used without limitation of type so long as such fluid can be moved by centrifugal force.

The platform 101 is rotated after the sample is injected. In various exemplary embodiments, the sample may be centrifuged based on centrifugal force generated during rotation. For this purpose, a sample separator 111 configured to centrifuge the sample may be formed in a lower part (i.e., a portion that is further from the center of rotation of the platform 101 than the position) of the sample chamber 110. When the injected sample is whole blood, the sample may be separated into a supernatant containing serum or plasma and a sediment such as blood cells. Once separated, the supernatant or sediment may then be transferred to the first reagent chamber 120 depending on the target material to be detected by the microfluidic device 100. In an exemplary embodiment, when the target material to be detected is a plasma protein, an upper part of the sample separator 111 is connected to the first reagent chamber 120 through the channel, thereby permitting the supernatant fluid to be transferred to the first reagent chamber 120.

As discussed above, the first reagent chamber 120 contains a primary capture conjugate that specifically binds to the target material in the sample, and activates generation of an electrochemical signal. The primary capture conjugate may be a conjugate of a primary capture material that specifically binds to the target material and an activity-inducing material configured to induce electrochemical activation of the signal material. The types of the capture material and the activity-inducing material depend on the types of the target material and the signal material.

After the sample is transferred to the first reagent chamber 120, the target material present in the sample specifically binds to the primary capture conjugate. Thereafter, the fluid in the first reagent chamber 120 is transferred to the reaction chamber 140 through the channel connected to the reaction chamber 140.

The reaction chamber 140 contains the secondary capture material that specifically binds to the target material. The secondary capture material may be coated on an inside wall of the reaction chamber 140, or be immobilized on a porous pad, a bead or a nano/micro-particle contained therein. For example, a bead on which the secondary capture material is immobilized may be a magnetic bead and the magnetic bead may be fixed within the reaction chamber 140 by a magnetic force supplied from the microfluidic test device 30. By immobilizing the second capture material on the bead or nano/micro-particle, the surface area in which the second capture material reacts with the target material is increased, thereby inducing efficient bonding.

Accordingly, when a signal material is supplied to the reaction chamber 140, an electrochemical signal is generated that is consistent in level to the amount of the target material contained therein. In order to reduce the detection of unbound activity-inducing material, a cleaning solution may be supplied to the reaction chamber 140 to remove the activity-inducing material which is not bonded to the target material before the signal material is injected into the reaction chamber 140.

Accordingly, a valve 135 disposed in the channel connecting the cleaning solution chamber 130 to the reaction chamber 140 is opened to transfer the cleaning solution to the reaction chamber 140 before the valve 155 of the second reagent chamber 150 opens. The cleaning solution removes impurities bonded to the secondary capture material and is transferred to a first waste solution chamber 160.

In this case, a general channel and valve may connect the reaction chamber 140 to the first waste solution chamber 160. However, as shown in the exemplary embodiment of FIG. 2, the channel 146 to connect the reaction chamber 140 to the first waste solution chamber 160 may be formed to have high flow resistance, thereby allowing the waste solution to be transferred without a separate valve operation. For example, the channel 146 may have a zigzag shape (as shown), have a width smaller than a general channel, have a length greater than a general channel, or may have a chamber disposed in the middle thereof.

As such, since the channel 146 connecting the reaction chamber 140 to the first waste solution chamber 160 may have a curved zigzag shape, it exhibits a higher flow resistance than a channel connecting the cleaning solution chamber 130 to the reaction chamber 140. In such a configuration, the waste solution is slowly transferred through the channel 146 to the first waste solution chamber 160 without separately operating a valve, after the reaction chamber 140 is completely filled with the cleaning solution.

After the reaction chamber 140 is cleaned, a solution containing the signal material is transferred from the second reagent chamber 150 to the reaction chamber 140. In the exemplary embodiment of FIG. 2, the second reagent chamber 150 is connected through the cleaning solution chamber 130 to the reaction chamber 140. However, the second reagent chamber 150 may be directly connected to the reaction chamber 150 without using another chamber disposed therebetween.

After washing, only the target material specifically bonded to the secondary capture material remains in the cleaned reaction chamber 140, while the primary capture conjugate containing the activity-inducing material is bonded to the target material. Accordingly, when the signal material is injected into the reaction chamber 140, the signal material is electrochemically activated by the activity-inducing material.

In an exemplary embodiment, the signal material may be a material that undergoes an oxidation/reduction reaction in the presence of the activity-inducing material. In this case, the electrochemically active reaction occurring in the reaction chamber 140 is an oxidation/reduction reaction. Thus, the amount of oxidized or reduced signal material changes depending on the amount of the target material present in the reaction chamber 140. More specifically, the relationship between the signal material and the activity-inducing material corresponds to the relationship between a substrate and an enzyme, and the activity-inducing material may serve as an oxidizing agent dehydrating the substrate. In this case, the electrochemically active reaction occurring in the reaction chamber 140 may be thought of as a biochemical reaction.

The oxidized or reduced signal material may be at least one of ferrocene, ferrocene derivatives, quinones, quinone derivatives, organic conductive salts, viologen, hexaammineruthenium (III) chloride, potassium ferrocyanide, dimethylferrocene (DMF), ferricinium, ferocene monocarboxylic acid, 7,7,8,8-tetracyanoquinodimethane (TCNQ)), tetrathiafulvalene (TTF), nickelocene (Nc), N,N-methylphenazinium (NMP+)) inobenzoic acid (MBTHDMAB)), 3-methyl-2-benzothiozolinone hydrazone, 2-methoxy-4-allylphenol, 4-aminoantipyrin (AAP), dimethylaniline, 4-aminoantipyrene, 4-methoxynaphthol, 3,3',5,5'-tetramethyl benzidine (TMB), 2,2-azino-di-[3-ethyl-benzthiazoline sulfonate], o-dianisidine, o-toluidine, 2,4-dichlorophenol, 4-amino phenazone, benzidine, and Prussian blue.

The signal generated from the electrochemically activated signal material is detected in the detection chamber 170. The microfluidic device 100 therefore separately includes a reaction chamber 140 in which an electrochemically active reaction of the signal material occurs, and a detection chamber 170 in which a signal is detected from the activated signal material, to prevent electrode contamination of the electrochemical sensor and improve detection sensitivity of the signal.

The reaction chamber 140 is connected to the detection chamber 170. When the valve 145 disposed in the channel between the reaction chamber 140 and the detection chamber 170 opens, the reaction solution is transferred to the detection chamber 170.

The detection chamber 170 includes a detector, such as an electrochemical sensor 180, to detect an electrochemical signal from the reaction solution. The electrochemical sensor 180 may include three types of electrodes, i.e., a working electrode, a reference electrode and a counter electrode, and configured to measure an electric signal generated by the oxidation/reduction reaction in the working electrode.

Materials used for the electrodes include, but are not limited to, silver, silver epoxy, palladium, copper, gold, platinum, silver/silver chloride, silver/silver ions, mercury/mercury oxide, conductive carbon, heavy metal oxides or the like and specific examples thereof include, for the reference electrode material, silver, silver epoxy, silver/silver chloride or silver/silver ions, for the working electrode material, conductive carbon, cobalt phthalocyanine paste, gold, platinum and palladium, and for the counter electrode material, conductive carbon, gold and platinum.

Methods for measuring signals by the electrochemical sensor 180 include an electric potential difference measurement method, a current measurement method, a voltage-current measurement method and the like. As such, the microfluidic device 100 may use any one of these methods.

The electrochemical sensor 180 includes a detection portion 181 which contacts the reaction solution and is configured to detect a signal, and a connection portion 182 which is configured to receive current from the outside and/or supply the detected signal to the outside. Since the detection portion 181 contacts the reaction solution, the detection portion 181 may be disposed inside the detection chamber 170, while the connection portion 182 may be disposed outside the detection chamber 170.

For example, as shown in FIG. 2, the electrochemical sensor 180 may be provided on a lower plate of the platform 101 and the detection chamber 170 may be formed on the detection portion 181. A detection area 171, within which the detection portion 181 is disposed, opens toward the electrochemical sensor 180, thereby bringing a solution in the detection chamber 170 into contact with the detection portion 181.

Also as shown in FIG. 2, the detection area 171 may be formed to have a larger width than an inlet or outlet of the detection chamber 170, thereby providing an efficient route for the reaction solution to contact the detection portion 181 without forming bubbles.

When the reaction solution is transferred to the detection chamber 170, the electrochemically activated signal material contained in the reaction solution contacts the working electrode of the detection portion 181. For example, when the signal material is oxidized, it receives electrons from the working electrode and is thus reduced. The microfluidic device 100 is therefore configured to measure a reduction current, thereby determining the presence or amount of the target material. For this purpose, the microfluidic test device 30 includes a controller configured to receive the signal detected and/or measured by the detector 180 and determine the presence and/or amount of the target material. The controller may also be configured to control movement of the microfluidic device 100 such as rotation of the microfluidic device 100 through the driver 31.

When detection of the detection chamber 170 is completed, the platform 101 rotates to transfer the reacted solution to the second waste solution chamber 190 and the channel 186 between the detection chamber 170 and the second waste solution chamber 190 is formed to have high flow resistance. However, this is given only as an exemplary embodiment, and any one of the channels of the microfluidic device 100 may have high flow resistance. On the other hand, any of the channels formed in the microfluidic device 100 may be a general channel, rather than a channel having high flow resistance.

FIGS. 3A to 3D illustrate materials contained in respective chambers and movement of the materials within the microfluidic device according to an exemplary embodiment.

FIGS. 3A to 3D illustrate only the sample chamber 110, a sample separator 111, the first reagent chamber 120, the second reagent chamber 150, the cleaning solution chamber 130 and the reaction chamber 140 in order to effectively show material movement between chambers, and movement of the material by operation of the microfluidic device 10 is supposed to be caused when microfluidic device 100 is mounted on the microfluidic test device 30.

Figure 3A:
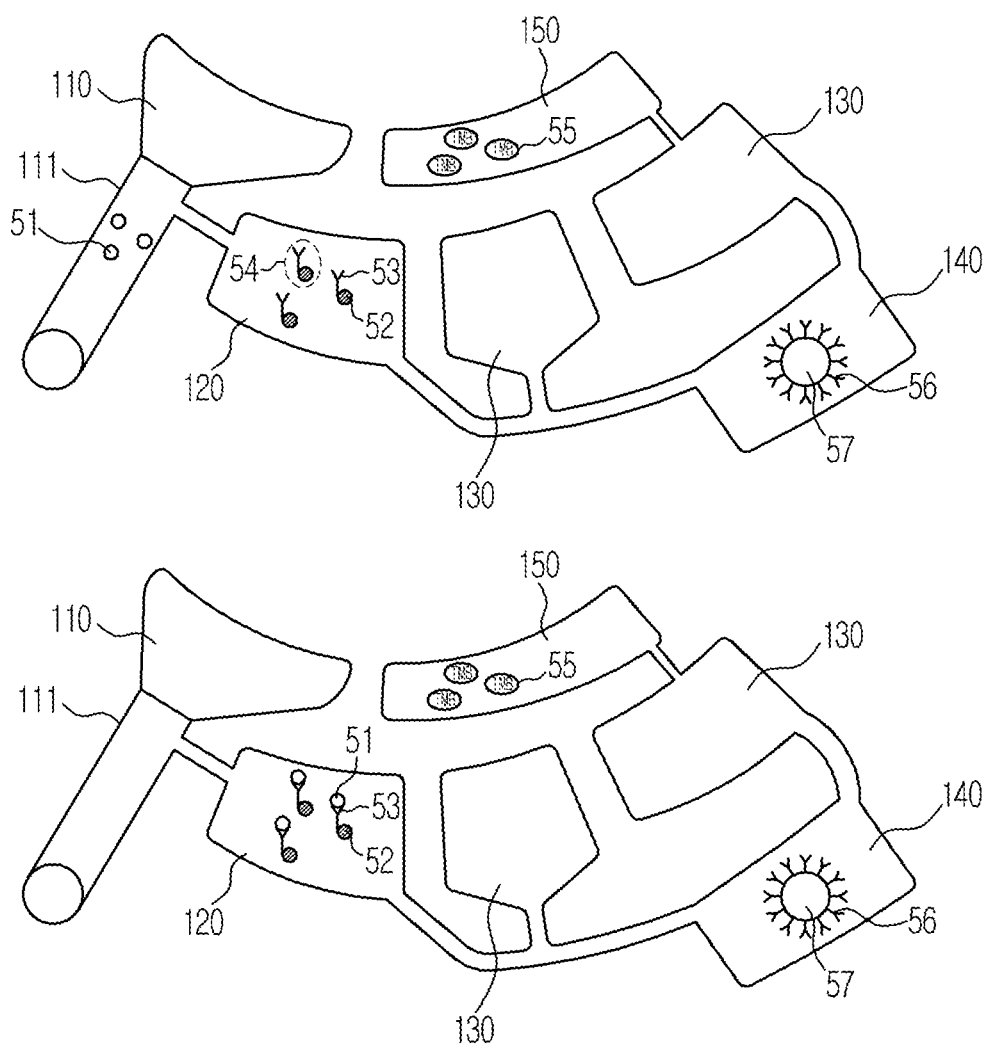
FIGS. 3A to 3D illustrate materials contained in respective chambers of the microfluidic device according to an exemplary embodiment, and movement of the materials therein.

In an exemplary embodiment, the microfluidic device 100 may be used for detection of C-reactive protein (CRP) present in a blood sample. As shown in FIG. 3A, when whole blood collected from a subject is injected into the sample chamber 110 and the platform 100 is rotated at, e.g., 3,600 RPM, whole blood is centrifuged in sample separator 111 to separate plasma from a sediment. The target material, CRP 51, is contained in the plasma.

Figure 3B:
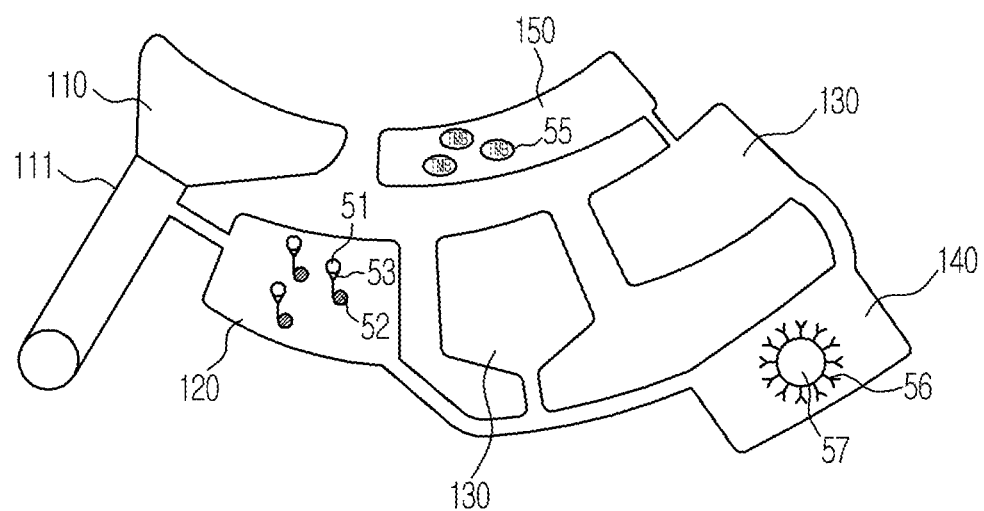

Referring to FIG. 3B, the centrifuged plasma is transferred to the first reagent chamber 120, which contains the primary capture conjugate 54 (see FIG. 3A). The primary capture conjugate 54 is a conjugate of the CRP antibody (first capture material, 53) and the electrochemical activity-inducing material 52. In the present exemplary embodiment, the activity-inducing material used is horseradish peroxidase (HRP), which is a type of peroxidase. When the plasma is transferred to the first reagent chamber 120, a bonding material of the primary capture conjugate 54 and the CRP 51 is formed through specific bonding between the CRP 51 present in plasma and the CRP antibody 53 of the primary capture conjugate 54.

The secondary capture material 56 is immobilized in the reaction chamber 140. For example, a CRP antibody (secondary capture material) that specifically binds to CRP may be immobilized on a bead that is immobilized within the reaction chamber 140. As described above in reference to FIG. 2, when the secondary capture material is immobilized on the bead, a greater surface area for reaction is provided.

Figure 3C:
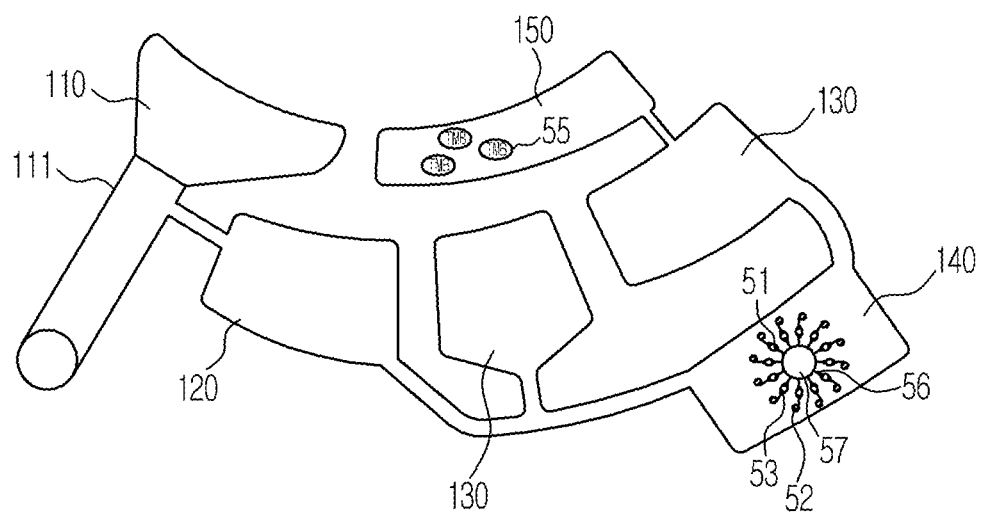

In addition, when the bonding material is supplied to the reaction chamber 140, as shown in FIG. 3C, the CRP 51 bonded to the primary capture conjugate 54 specifically binds to the secondary capture material 56.

In addition, as described above, in order to remove any unbound activity-inducing material and/or any material that is not specifically bound to the secondary capture material, the valve between the cleaning solution chamber 130 and the reaction chamber 140 opens and the reaction chamber 140 is washed.

Figure 3D:
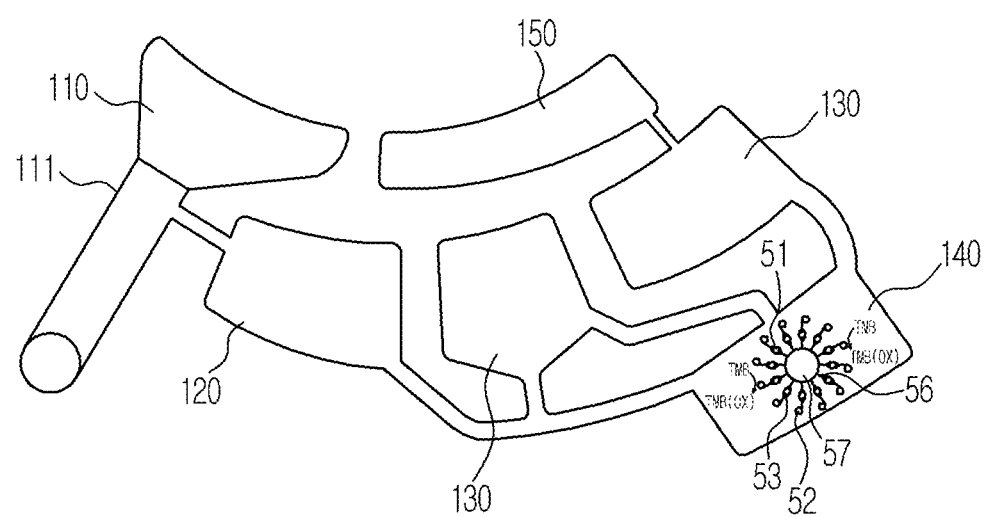

Referring to FIG. 3C, the second reagent chamber 150 accommodates a solution containing the signal material 55. In the present exemplary embodiment, the second reagent chamber 150 contains a TMB solution. After the reaction chamber 140 is washed, the TMB solution is allowed to flow into the reaction chamber 140, as shown in FIG. 3D, resulting in an electrochemical activation reaction of the TMB 55 by the activity-inducing material 52. More specifically, the TMB 55 flowing into the reaction chamber 140 is oxidized by the HRP 52 and is thus converted into TMB (ox).

As discussed above, when the reaction solution is transferred to the detection chamber 180, detection of the signal occurs in the detection chamber 180. In an exemplary embodiment, oxidized TMB contained in the reaction solution receives electrons from the working electrode of the electrochemical sensor 180 and is reduced. As such, the amount of CRP may be estimated by measuring this reduction current.

Figure 4:
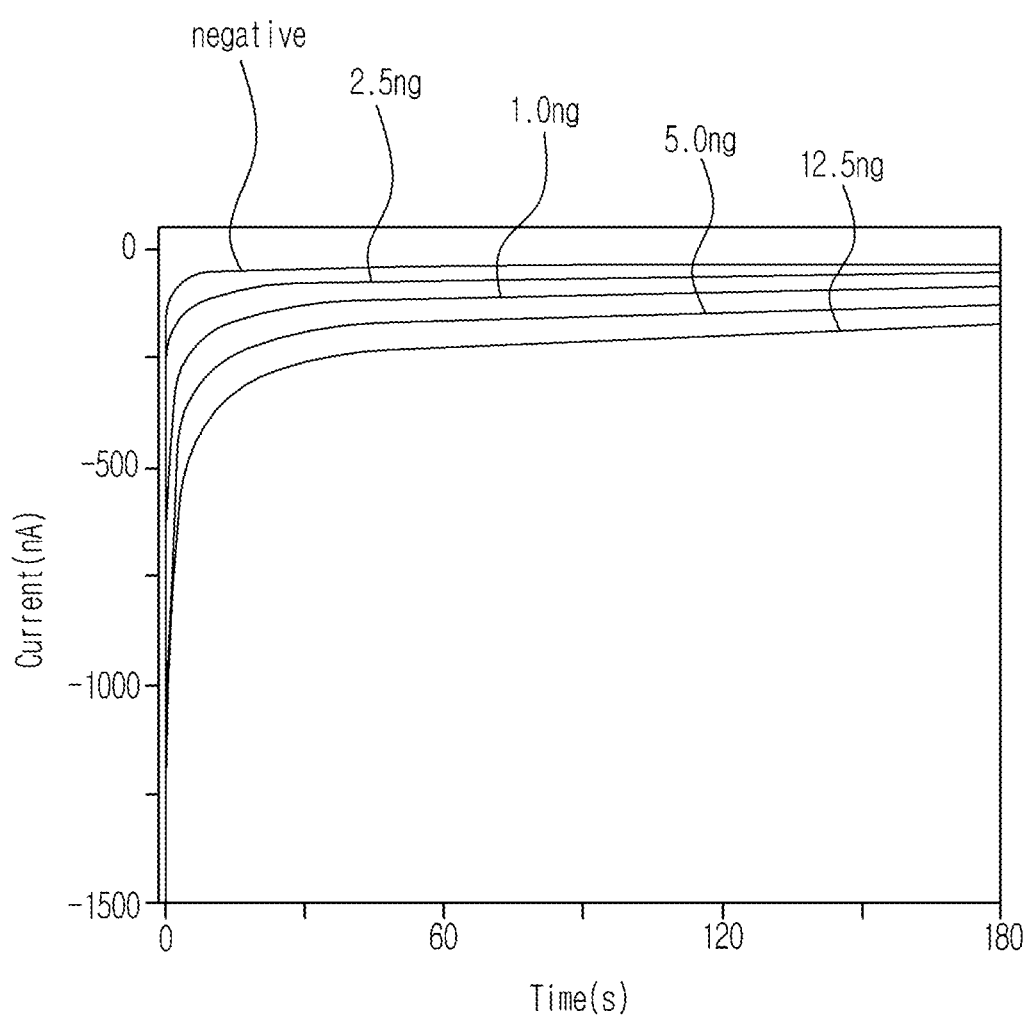
FIG. 4 illustrates a graph showing detection results using the microfluidic device according to an exemplary embodiment.

FIG. 4 illustrates a graph showing detection results using the microfluidic device according to an exemplary embodiment. The graph of FIG. 4 shows a signal measured using a current measurement method, when the platform 101 stops after a reaction solution is transferred to the detection chamber 170.

It can be seen from FIG. 4 that as the concentration of the target material increases, the absolute value of a measured current increases. Accordingly, the controller of the microfluidic test device 30 may be configured to estimate the concentration of the target material from a level of the signal measured using the microfluidic device 100.

Hereinafter, the microfluidic test device and a microfluidic system including the same will be described in detail.

Figure 5:
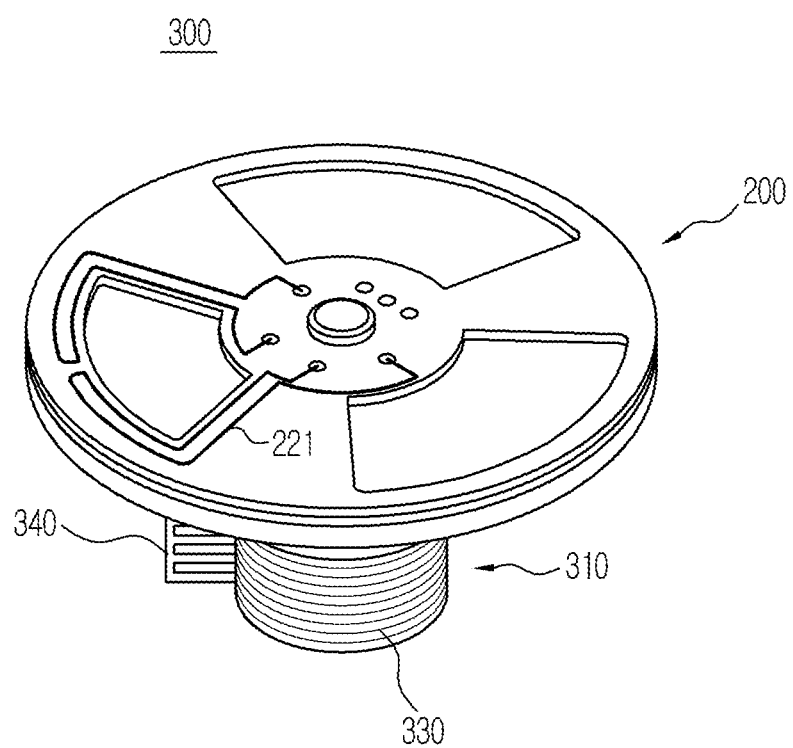
FIG. 5 is a perspective view illustrating an exterior appearance of a driver of a microfluidic test device according to an exemplary embodiment and a microfluidic device mounted on the microfluidic test device.

FIG. 5 is a perspective view illustrating an exterior appearance of a driver of a microfluidic test device according to an exemplary embodiment and a microfluidic device mounted on the microfluidic test device.

The microfluidic test device 300 rotates the microfluidic device 200 and is configured to detect the presence and/or amount of the target material in a fluid sample. The microfluidic test device 300 includes a driver 310 configured to rotate the microfluidic device 200, and the driver 310 includes a motor.

When the microfluidic device 200 is mounted on the microfluidic test device 300, such a configuration constitutes one microfluidic system, since the microfluidic test device 300 and the microfluidic device 200 are considered to be part of a system capable of detecting target materials in the fluid sample.

When the microfluidic device 200 is used to detect a target material by an electrochemical method, transmittance and reception between the microfluidic device 200 and the microfluidic test device 300 are required. In addition, as described below, a structure capable of measuring the signal is required when the microfluidic device 200 rotates and electricity is supplied thereto. In an exemplary embodiment, as shown in FIG. 5, current supply and signal readout are possible by providing a slip ring 330 contacting a brush 340 in a rotor of the motor 310 and bringing the microfluidic device 200 mounted on the microfluidic test device 300 into electrical contact with the slip ring 330.

Figure 6:
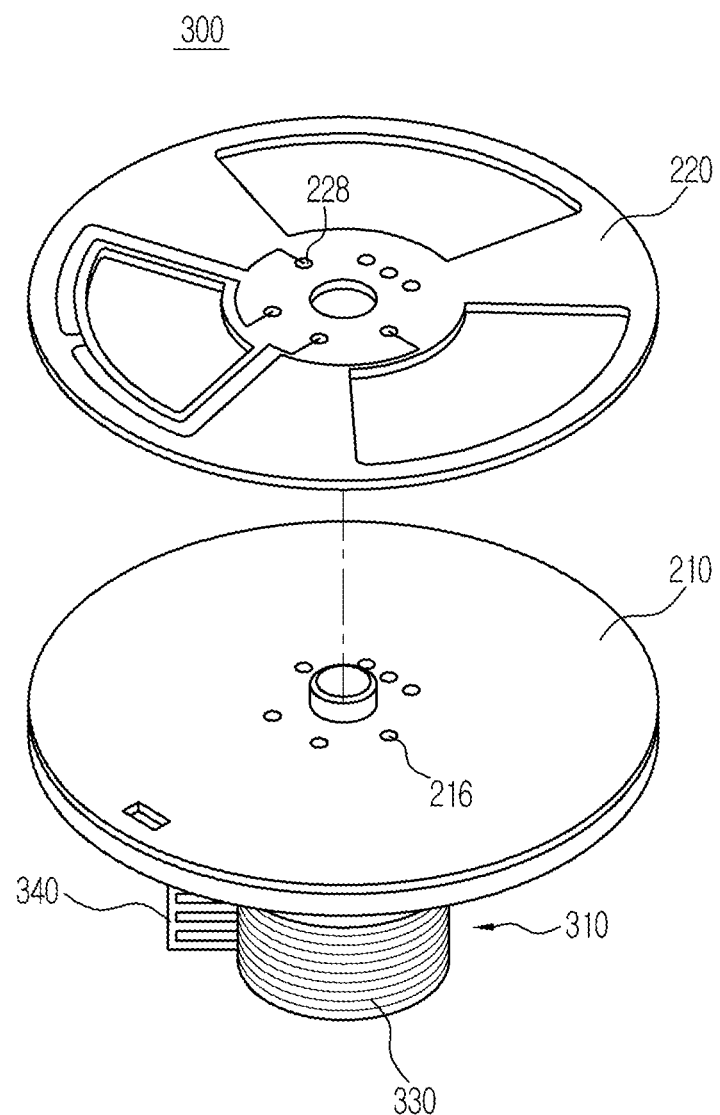
FIGS. 6 and 7 are exploded perspective views illustrating a microfluidic device mounted on the microfluidic test device according to an exemplary embodiment.
Figure 7:
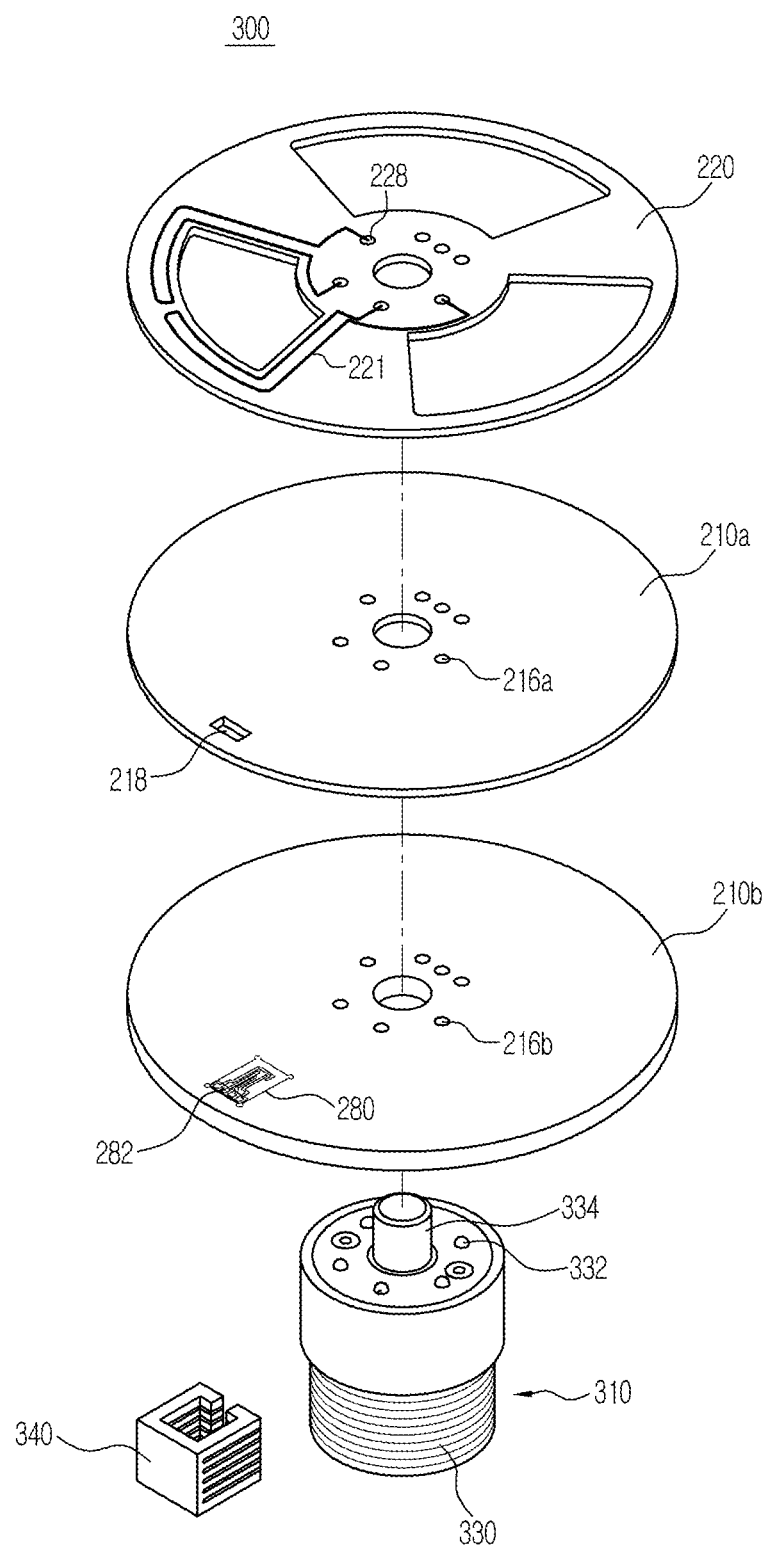

FIGS. 6 and 7 are exploded perspective views illustrating a microfluidic device mounted on the microfluidic test device according to an exemplary embodiment.

Referring to FIGS. 6 and 7, the microfluidic test device 300 may include a printed circuit board (PCB) 220 on the platform 210 to bring the microfluidic device 200 into electrical contact with the slip ring 330. The motor contacting a lower surface of the platform 210 includes a first contact pin 332 to enable the microfluidic device 200 to electrically contact the slip ring 330. The platform 210 includes a pin hole 216a or 216b formed in a region corresponding to the first contact pin 332, when an axis 334 of the motor is inserted into the center of the platform 210. In addition, a second contact pin corresponding to the pin hole 216a or 216b is formed in a lower part of the PCB 220 and electrically contacts the first contact pin through the pin hole.

A window 218 is formed in the upper plate 210a of the platform 210 and disposed in a region corresponding to a connection portion 282 of the electrochemical sensor 280 of the lower plate 210b. A connection wire 221 formed in the PCB 220 electrically connects the first contact pin 332 to the connection portion 282 of the electrochemical sensor.

Based on the structure described above, the microfluidic test device 300 is configured to supply electricity while rotating the microfluidic device 200 and acquires detection results therefrom. Specifically, the controller is configured to control overall operation of the microfluidic test device 300 and rotates the microfluidic device 200 while controlling the driver 310. At the same time, the controller supplies electricity through the slip ring 330 to the electrochemical sensor 280 and acquires a signal from the electrochemical sensor 280. In addition, the controller is configured to determine the presence and/or amount of the target material from the acquired signal.

It should be understood that the microfluidic device 200 mounted on the microfluidic test device 300 may be the microfluidic device 100 described above. When the microfluidic device 100 is mounted on the microfluidic test device 300, the microfluidic test device 300 supplies electricity to the electrochemical sensor 180 while rotating the microfluidic device 100, and acquires a signal from the electrochemical sensor 180.

Hereinafter, a result obtained from the microfluidic device 200 mounted on the microfluidic test device 300 will be described in detail.

Figure 8:
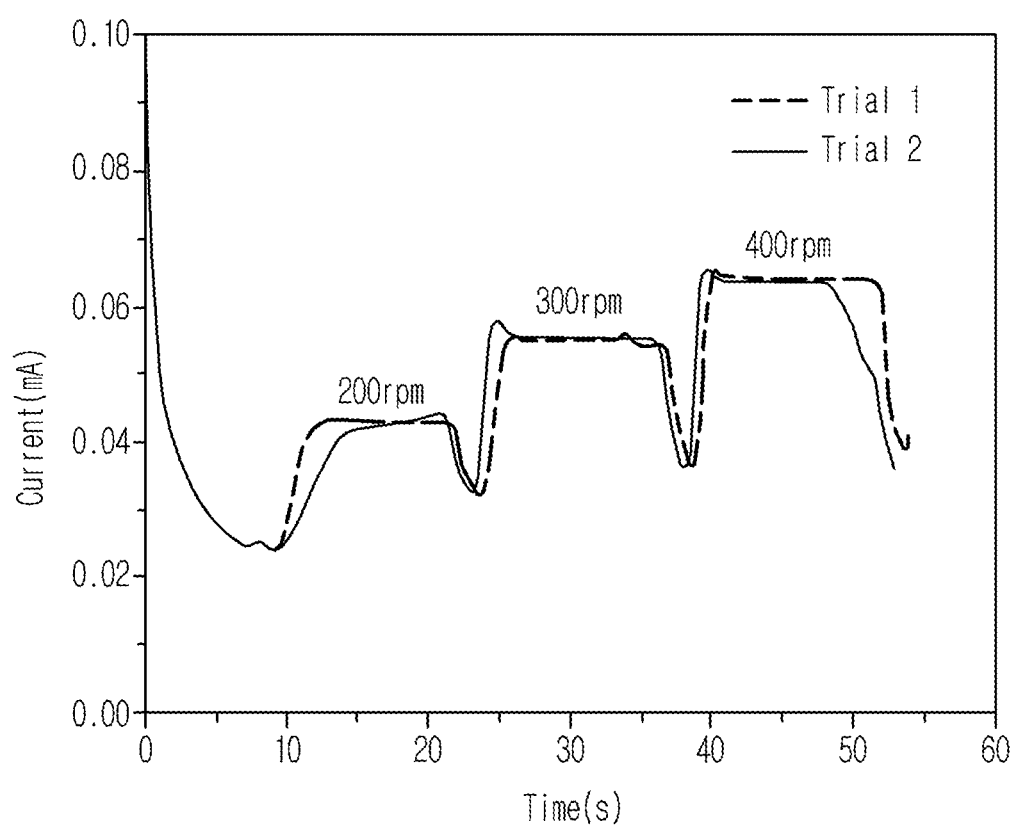
FIG. 8 is a graph showing signals acquired while changing a rotation speed of the exemplary microfluidic device.
Figure 9:
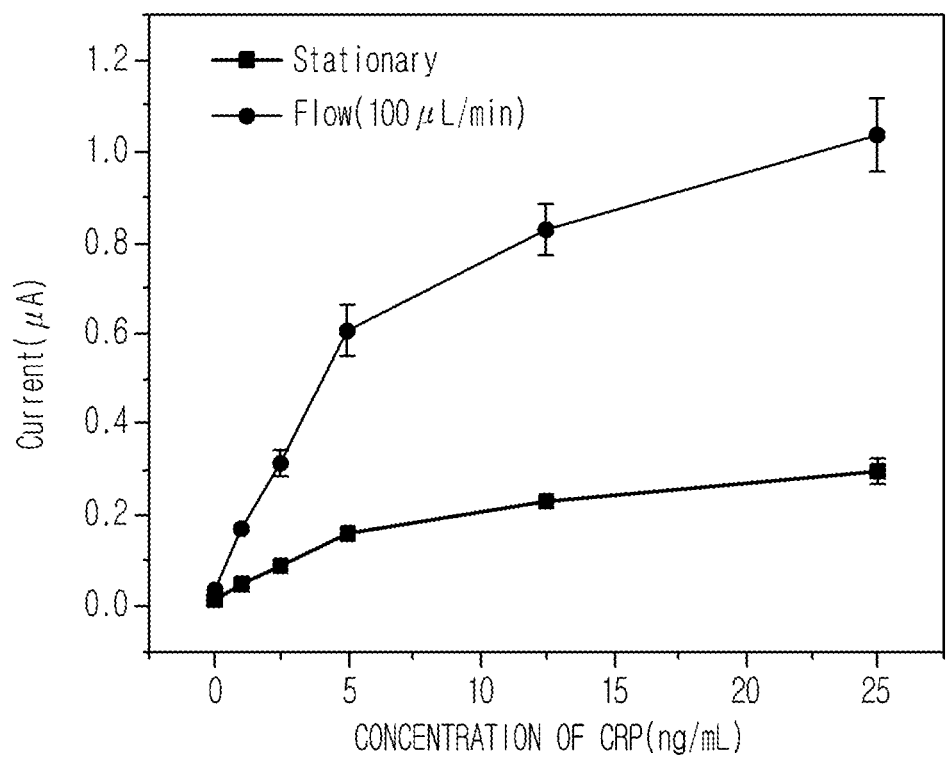
FIG. 9 is a graph showing the signal acquired when the exemplary microfluidic device stops and the signal acquired when the microfluidic device rotates.

FIG. 8 is a graph showing signals acquired while changing the rotation speed of the microfluidic device. FIG. 9 is a graph showing a signal acquired when the microfluidic device stops rotating and a signal acquired when the microfluidic device rotates.

While the microfluidic device 100 is mounted on the microfluidic test device 300, the microfluidic test device 300 supplies electricity to the electrochemical sensor 180. The microfluidic test device 300 continues to rotate the microfluidic device 100 even after the reaction solution is transferred to the detection chamber 170, and a signal is measured through the connection portion 182.

Referring to FIG. 8, signals are measured at different rotational speeds of 200 rpm, 300 rpm and 400 rpm. As a result, compared with the signal of FIG. 4 measured while the microfluidic device 100 is stopped, as rotational speed of the microfluidic device 100 increases, the level of the signal increases.

The graph of FIG. 9 shows signal measurement results in stopped and rotational states (100 μL/min) while changing the concentration of the target material, CRP. Referring to FIG. 9, when the microfluidic device 100 is in the stopped state, although the concentration of the target material increases, the level of the measured signal does not greatly change. That is, detection sensitivity is not high. However, when the microfluidic device 100 is rotated, the flow rate of the reaction solution passing through the detection portion 181 is set at 100 μL/min and the level of the measured signal greatly increases, as compared to the stop state, as the concentration of the target material increases. Accordingly, from the result shown in the graph of FIG. 9, it can be seen that when the microfluidic device 100 rotates, there is a higher sensitivity for measured signals.

Furthermore, when signals are measured while rotating the microfluidic device 100, the electrode surface of the electrochemical sensor 180 is continuously cleaned, thereby increasing reproducibility of the measured signal.

In the afore-mentioned exemplary embodiment, the microfluidic test device 300 includes the slip ring shown in FIGS. 5 to 7, and the microfluidic device 200 mounted on the microfluidic test device 300 is the microfluidic device 100 shown in FIG. 2. However, this is given only as an exemplary embodiment.

The microfluidic test device 300 may have any structure, rather than a structure having a slip ring, so long as the microfluidic test device 300 is configured to supply electricity to the electrochemical sensor and measure a signal while rotating the microfluidic device 200.

In addition, the microfluidic device 200 may have any structure so long as it is capable of detecting an electrochemical signal using the electrochemical sensor. Thus, the structure of the microfluidic device 100 shown in FIG. 2, in which the electrochemically active reaction and signal detection separately occur in different chambers, is provided for exemplary purposes only.

As discussed above, the flow rate of the reaction solution contacting the electrochemical sensor affects a level of the measured signal. Accordingly, the flow rate is measured from the level of the measured signal in accordance with Equation 1 as follows.

$$i = 1.47nFC(DA/B)^{2/3}v^{1/3}$$ [Equation 1]

wherein i represents a level of measured current, n represents kinematic viscosity, F represents Faraday's constant, D represents a diffusion coefficient, A represents an electrode area, B represents a height of a detection chamber, and v represents a flow rate of a fluid. Accordingly, the controller of the microfluidic test device 300 is configured to calculate the flow rate of reaction solution passing through the electrochemical sensor by applying a measured current level and various constants to Equation 1.

Figure 10:
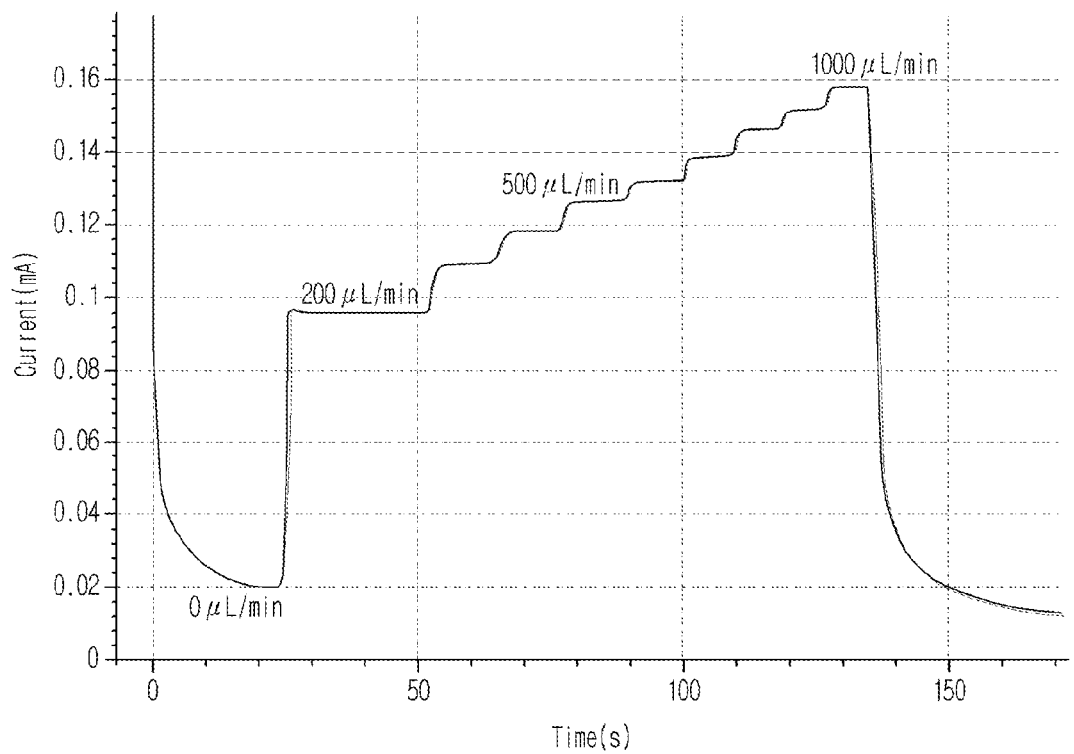
FIG. 10 is a graph showing signals measured while changing a flow rate.
Figure 11:
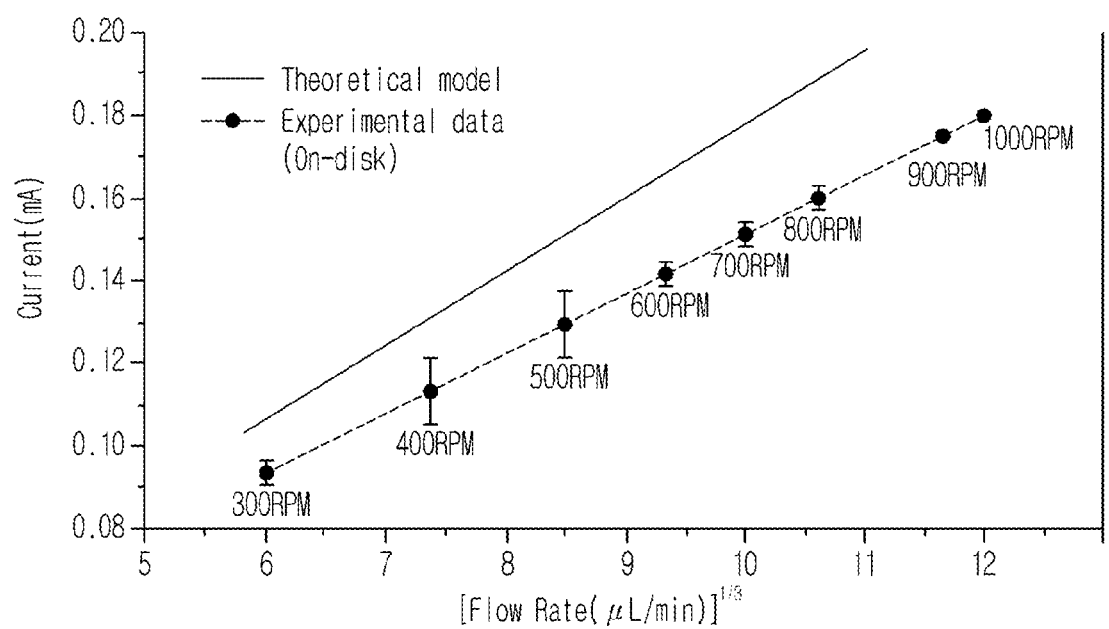
FIG. 11 is a graph comparing signals measured while changing a rotation speed of the exemplary microfluidic device with theoretical data.

FIG. 10 is a graph showing signals measured at different flow rates. FIG. 11 is a graph comparing signals measured while changing the rotational speed of the microfluidic device with theoretical data.

The graph of FIG. 10 shows measurement results of signals from the electrochemical sensor 180 while flow rates of the reaction solution passing through the electrochemical sensor 180 sequentially increase from 200 μL/min, 500 μL/min, and 1,000 μL/min. It can be seen from FIG. 10 that the level of the detected signal increases as flow rate increases, and a flow rate is high when a measured signal level is high.

The graph of FIG. 11 shows signal data measured from the electrochemical sensor 180 as flow rate is increased by increasing a rotation speed (RPM) of the microfluidic device 200, and theoretical data corresponding thereto. It can be seen from the experimental data that, as the rotational speed (RPM) of the microfluidic device 200 increases, the flow rate increases, thereby increasing the measured signal level, as described above. The relationship between the flow rate and the signal shown in the experimental data substantially corresponds to that of the theoretical data, thereby confirming accuracy of the estimated flow rate of the reaction solution based on the measured current level.

The electrochemical sensor may be mounted on any channel or chamber provided in the microfluidic device 200. In addition, when a signal is measured during fluid flow within the channel or chamber on which the electrochemical sensor is mounted, the controller is configured to calculate the flow rate from the measured signal and determine the relationship between fluid flow rate and the rotational speed of the microfluidic device 200.

From the experimental results shown in FIGS. 10 and 11, as the flow rate of fluid passing through the electrochemical sensor increases, the level of the detected signal increases. Thus, the microfluidic device 200 may include chamber or channel for controlling flow rate, which includes an electrochemical sensor mounted on the other chamber or channel, in addition to the detection chamber. In an exemplary embodiment, the controller is configured to measure a signal from the electrochemical sensor mounted on the chamber or channel for controlling a flow rate and calculate a flow rate before the signal is measured from the electrochemical sensor mounted on the detection chamber. The controller may then increase the rotational speed of the microfluidic device 200 to enable the detection chamber to detect the signal under optimum conditions, when the calculated flow rate is less than a predetermined reference value.

Hereinafter, a method for controlling the microfluidic test device according to an exemplary embodiment will be described.

Figure 12:
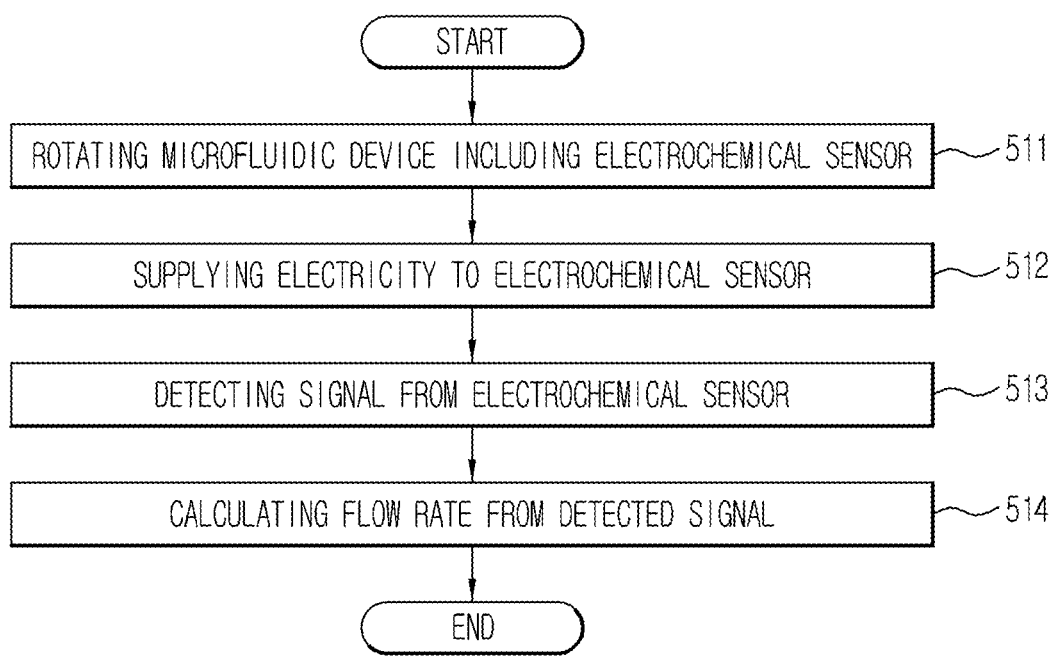
FIG. 12 is a flowchart illustrating a method for calculating a flow rate within the microfluidic test device according to an exemplary embodiment.

FIG. 12 is a flowchart illustrating a method for calculating flow rate within the microfluidic test device according to an exemplary embodiment.

A microfluidic device including an electrochemical sensor is mounted on the microfluidic test device. The electrochemical sensor may be mounted on the detection chamber to detect a signal corresponding to the target material or on any channel or chamber provided in the microfluidic device.

Referring to FIG. 12, first, the mounted microfluidic device is rotated (511). The microfluidic test device includes a driver including a motor and the rotational axis of the motor is inserted into the rotational center of the microfluidic device, thereby enabling the microfluidic device to rotate when the motor is rotated. When the microfluidic device is rotated, the fluid is transferred based on centrifugal force.

In addition, electricity is supplied to the electrochemical sensor (512). For this purpose, the microfluidic test device has a structure capable of supplying electricity the microfluidic device while rotating. This has been described above and a detailed explanation thereof is thus omitted. When electricity is supplied to the electrochemical sensor, a signal material passing through the electrochemical sensor causes an electrochemical reaction, thereby generating a signal.

The signal generated from the electrochemical sensor is detected (513) and a flow rate is calculated from the detected signal (514). The calculation of flow rate may be carried out using Equation 1 described above.

Figure 13:
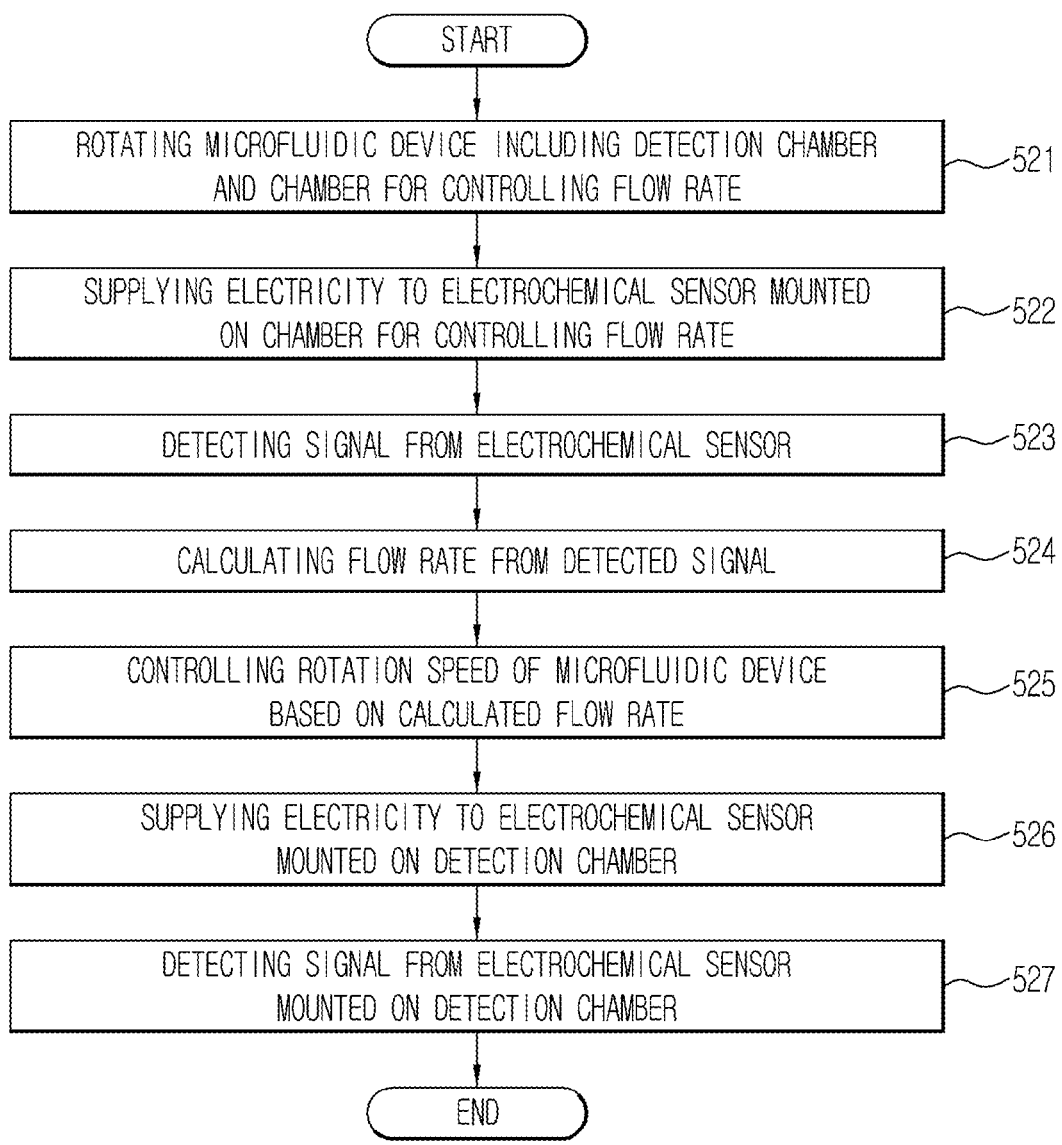
FIG. 13 is a flowchart illustrating a method for controlling a flow rate of a fluid flowing in the microfluidic device according to an exemplary embodiment of the present invention.

FIG. 13 is a flowchart illustrating a method for controlling a flow rate of fluid flowing within the microfluidic device according to an exemplary embodiment.

The microfluidic device includes a detection chamber used for detection of the target material, and a chamber or channel for controlling a flow rate, and is mounted on the microfluidic test device. For convenience of description of the present exemplary embodiment, a chamber for controlling flow rate is shown. Both the detection chamber and the chamber for controlling a flow rate include an electrochemical sensor. An electrochemical signal is generated when an electrochemically activated signal material is supplied to both the detection chamber and the chamber for controlling a flow rate.

First, a microfluidic device including the detection chamber and the chamber for controlling a flow rate is rotated (521). When the microfluidic device is rotated, a fluid within the microfluidic device is moved based on centrifugal force.

Electricity is supplied to the electrochemical sensor mounted on the chamber for controlling flow rate (522). In addition, when the electrochemically activated signal material is supplied to the chamber for controlling flow rate, an electrochemical signal is generated and the signal is detected (523).

A flow rate is calculated from the detected signal (524). The calculation of the flow rate may be carried out using Equation 1 described above and a rotational speed of the microfluidic device may be controlled based on the calculated flow rate (525). For example, a rotational speed of the microfluidic device may be increased when the present flow rate is lower than a predetermined reference value, based on the factor that when the flow rate of fluid passing through the electrochemical sensor increases, detection sensitivity of the signal is improved. Electricity is supplied to the electrochemical sensor provided in the detection chamber (526). However, it should be understood that the supply of electricity to the chamber for controlling flow rate and to the detection chamber are not necessarily separately performed. If desired, electricity may be simultaneously supplied to both of the electrochemical sensors of the two chambers.

A signal is detected from the electrochemical sensor mounted on the detection chamber (527). The detection of the signal is performed while the rotation speed of the microfluidic device is controlled. The detection sensitivity of the signal is thought to be improved. In addition, the presence and/or amount of the target material in the fluid sample may be determined using the detected signal.

According to a microfluidic device and a microfluidic system of an exemplary embodiment, an inherent surface of a sensor is used for detection by physically separating a chamber in which reactions occur from a chamber in which electrochemical sensing occurs, and accurate results with high sensitivity may be obtained by detecting signals in a fluid flow state created by rotating the microfluidic device.

According to a microfluidic system and a microfluidic test device of another exemplary embodiment, a flow rate of a fluid which passes through an electrochemical sensor may be calculated using a detected signal.

Although a few exemplary embodiments have been shown and described, it would be appreciated by those skilled in the art that changes may be made in these exemplary embodiments without departing from the principles and spirit of the inventive concept, the scope of which is defined in the claims and their equivalents.

What is claimed is:

1. A microfluidic device comprising a rotatable platform, wherein the platform comprises:
    a sample chamber to which a sample is supplied;
    a first reagent chamber;
    a first capture conjugate disposed in the first reagent chamber and configured to capture a target material contained in the sample;
    a second reagent chamber;
    a signal material disposed in the second reagent chamber and configured to be induced to have electrochemical activity by the first capture conjugate;
    a reaction chamber providing an area in which a biochemical reaction between the sample and the signal material supplied occurs when the platform rotates;
    a second capture material immobilized within the reaction chamber and configured to capture the target material such that the target material and the first capture conjugate are immobilized within the reaction chamber;
    a detection chamber separated from the reaction chamber, the detection chamber comprising a detector configured to detect an electrochemical signal generated by the signal material which moves to the detection chamber from the reaction chamber; and
    a plurality of channels connecting the chambers.

2. The microfluidic device according to claim 1, wherein the first capture conjugate is a conjugate of a first capture material configured to capture the target material and an activity-inducing material configured to induce electrochemical activity of the signal material.

3. The microfluidic device according to claim 1, wherein the second capture material is immobilized on an inner wall of the reaction chamber.

4. The microfluidic device according to claim 1, wherein the second capture material is immobilized on a bead or particle disposed within the reaction chamber.

5. The microfluidic device according to claim 1, wherein the signal material is a material which is oxidized or reduced by the activity-inducing material.

6. The microfluidic device according to claim 1, wherein the detector comprises a plurality of electrodes and an electrochemical sensor configured to detect an electrochemical signal from an oxidation/reduction reaction occurring in at least one of the electrodes.

7. The microfluidic device according to claim 6, wherein the detector comprises:
    a detection portion contacting a reaction solution flowing in the detection chamber and configured to detect an electrochemical signal; and
    a connection portion configured to transfer the electrochemical signal detected by the detection portion to the outside.

8. The microfluidic device according to claim 7, wherein the detection portion is disposed in the detection chamber and the connection portion is disposed outside the detection chamber.

9. The microfluidic device according to claim 8, wherein the detection portion of the detection chamber has a width which is greater than a width of an inlet through which the reaction solution is supplied, and greater than a width of an outlet through which the reaction solution is discharged.

10. The microfluidic device according to claim 1, wherein at least one of the channels has a shape providing a high flow resistance.

* * * * *